(12) United States Patent
Sanders et al.

(10) Patent No.: US 6,378,149 B1
(45) Date of Patent: Apr. 30, 2002

(54) RADIOLUCENT SPLIT-LEG ACCESSORY FOR A SURGICAL TABLE

(75) Inventors: Ward L. Sanders, Albion, PA (US); Roger J. Malcolm, Dana Point, CA (US)

(73) Assignee: Steris INC, Temecula, CA (US)

( * ) Notice: Subject to any disclaimer, the term of this patent is extended or adjusted under 35 U.S.C. 154(b) by 0 days.

(21) Appl. No.: 09/491,494

(22) Filed: Jan. 25, 2000

Related U.S. Application Data
(60) Provisional application No. 60/117,170, filed on Jan. 25, 1999.

(51) Int. Cl.⁷ ............................................. A61G 13/12
(52) U.S. Cl. ...................... 5/624; 5/648; 5/601; 5/619; 378/209
(58) Field of Search ............................ 5/601, 619, 621, 5/624, 648, 650, 651; 378/209

(56) References Cited

U.S. PATENT DOCUMENTS

| | | | |
|---|---|---|---|
| 3,227,440 A | * | 1/1966 | Scott .............................. 5/619 |
| 3,486,747 A | * | 12/1969 | Cardoso ......................... 5/619 |
| 4,103,170 A | * | 7/1978 | Spradlin ........................ 5/619 |
| 4,225,127 A | * | 9/1980 | Strutton ......................... 5/624 |
| 4,529,185 A | | 7/1985 | Gutierres |
| 4,552,346 A | | 11/1985 | Schnelle et al. |
| D287,625 S | | 1/1987 | Brendgord et al. |
| 4,681,308 A | * | 7/1987 | Rice ............................... 5/624 |
| 4,698,837 A | * | 10/1987 | Van Steenburg ........... 5/601 X |
| 4,717,133 A | | 1/1988 | Walsh et al. |
| 4,872,656 A | | 10/1989 | Bredngord et al. |
| 4,989,848 A | | 2/1991 | Monroe |
| 5,214,812 A | * | 6/1993 | Bartow et al. ................. 5/624 |
| 5,560,577 A | | 10/1996 | Keselman |
| 5,645,079 A | | 7/1997 | Zahiri et al. |
| 5,771,513 A | | 6/1998 | Kirchgeorg et al. |
| 5,802,641 A | | 9/1998 | Van Steenburg |

FOREIGN PATENT DOCUMENTS

| | | | | |
|---|---|---|---|---|
| CA | 997407 | * | 9/1976 | .................... 5/619 |
| DE | 44 06 553 C1 | | 3/1994 | |
| EP | 0 845 254 A2 | | 10/1997 | |

* cited by examiner

*Primary Examiner*—Michael F. Trettel
(74) *Attorney, Agent, or Firm*—Fay, Sharpe, Fagan, Minnich & McKee, LLP (57) ABSTRACT

An accessory (26,28) for selectively coupling with an orthopedic table (A) supports a patient's leg during surgery. The accessory includes a unitary support member (42) formed from a radiolucent material, such as carbon fiber. A joint assembly (40) pivotably and removably mounts the accessory to a side rail (24) of the table.

17 Claims, 13 Drawing Sheets

RADIOLUCENT SPLIT-LEG ACCESSORY FOR A SURGICAL TABLE

This application claims the priority of U.S. Provisional Application Ser. No. 60/117,170, filed Jan. 5, 1999.

Background of the Invention

The present invention relates to the surgical table arts. It finds particular application in connection with a removable accessory with a radiolucent support surface for the positioning of a patient's legs during surgery, and will be described with particular reference thereto. It should be appreciated, however, that the accessory is also suited to the support of a patient's arms or for use in forensic or veterinary applications.

For performing many modern surgical procedures, a support, such as a table, is used for positioning the patient on whom the procedures are to be performed. The table preferably provides unrestricted access by a surgeon to the parts of the patient's body on which the surgical procedures are to be performed. The table should also permit positioning of image-amplification apparatus proximate those parts of the patient's body on which the surgeon is to perform surgical procedures.

Conventional surgical tables include a horizontal support for the upper body of the patient, a base for supporting the upper body support a suitable distance from the floor, and a leg support, connected to the upper body support, for supporting the legs. For certain types of surgery, such as laparoscopic surgery, where the surgeon requires access to the pelvic region of the patient, or where the surgeon is operating on the legs, such as knee arthroscopy, vascular surgery, and orthopedic surgery, the table includes abductor bars, rather than a leg support, for maintaining the patient's legs in a spaced position. This allows the surgeon to stand between the patient's legs to conduct the surgery. The abductor bars are usually mounted to the base for horizontal pivotal movement and include foot supports which are clamped to the bars. The foot supports are moved along the abductor bars to accommodate patients of different sizes. U.S. Pat. Nos. 4,872,656; 4,989,848; and Des. 287,625 provide examples of such tables.

Some surgical procedures employ image-amplification apparatus to provide the surgeon with a picture of the operation in progress. Examples include fluoroscopic imaging and x-ray imaging. It is desirable for the surgical table to provide the source of radiation with 360 degree access to the site of the operation in such procedures. Typically, leg supports and abductor bars are formed from materials which are not radiolucent, i.e. they limit access to x-rays and other radiation used to monitor the surgical procedures. Additionally, such supports are often only pivotable in a horizontal direction and thus the image amplification equipment is not able to encircle completely one of the legs.

There remains a need for a leg support which provides access to the patient for surgery while providing all-round access to monitoring equipment. The present invention provides a radiolucent split-leg accessory for a surgical table which overcomes the above-referenced problems and others.

SUMMARY OF THE INVENTION

In accordance with one aspect of the present invention, a surgical table for supporting a patient during the performance of a surgical procedure is provided. The table includes a base and a table top mounted on the base for supporting an upper portion of the patient's body. The table includes at least one leg support sub-assembly, pivotally mounted to the table top. The leg support sub-assembly includes a support member for supporting a patient's leg. The support member includes a support surface formed from a radiolucent material. A mounting member pivotally connects the support member to the table top.

In accordance with another aspect of the present invention, an accessory for a surgical table is provided. The accessory includes a support member for supporting a patient's leg. The support member includes a support surface formed from a radiolucent material, which supports upper and lower portions of the patient's leg. A mounting member selectively mounts the support member to the surgical table and enables selective pivoting of the support member relative to the table.

In accordance with another aspect of the present invention, an accessory for a surgical table is provided. The accessory includes a support member which defines a trough configured for receiving upper and lower portions of a patient's leg. A mounting assembly, connected with the support member, is provided for selectively locking the support member in a plurality of positions relative to the table. The mounting assembly is selectively releasable to enable free motion of the support member.

One advantage of the present invention is that it provides a support for a patient's legs during surgery.

Another advantage of the present invention is that it is radiolucent.

Yet another advantage of the present invention is that it cradles a patient's legs.

A further advantage of the present invention is that it permits independent horizontal and vertical positioning of a patient's legs.

A yet further advantage of the present invention is that it is readily connected to the side rail of a conventional surgical table.

A still further advantage of the present invention is that it permits a conventional surgical table to be readily converted to a split-leg table.

Still further advantages of the present invention will become apparent to those of ordinary skill in the art upon reading and understanding the following detailed description of the preferred embodiment.

BRIEF DESCRIPTION OF THE DRAWINGS

The invention may take form in various components and arrangement of components and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
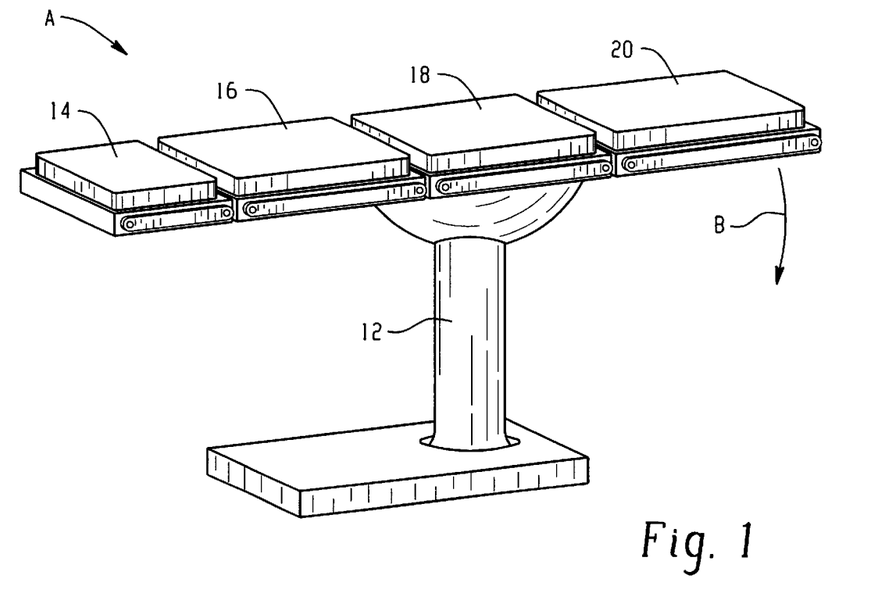
FIG. 1 is a perspective view of a surgical table prior to attachment of a split leg accessory.
Figure 2:
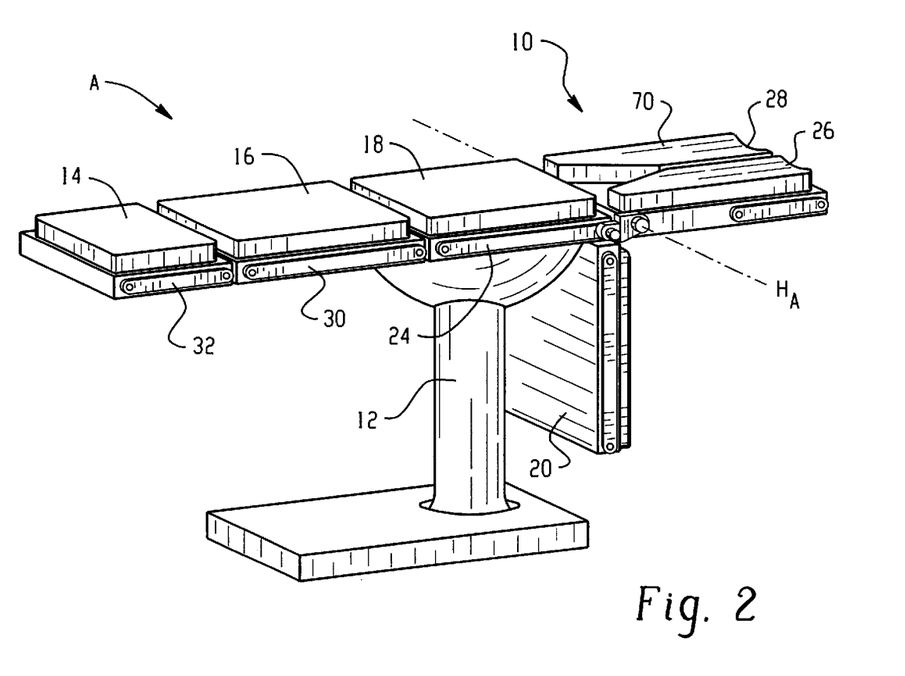
FIG. 2 is a perspective view of the surgical table of FIG. 1 with a leg support section of the table pivoted out of the way and a split-leg accessory connected to the table according to the present invention.

With reference to FIGS. 1 and 2, a surgical table A of the type suited for attachment of a split-leg accessory 10 is shown. The table includes a base 12 for positioning the table at a selected height above a floor surface and a number of connected support sections. As shown in FIG. 1, the table includes a head section 14, for supporting the head of the patient, an upper body support section 16, for supporting the patient's upper body, a lower body support section 18, for supporting the patient's pelvic region, and a leg support section 20, for supporting the patient's legs when the slit-leg accessory is not in use, although fewer or greater support sections are also contemplated. The leg section 20 is pivotally connected to the lower body section 18 and the head section 14 is pivotally connected to the upper body section 16 for pivotal movement about a horizontal axis. As shown in FIG. 1, the table sections are in a level position, with the leg support section extending generally horizontally from the lower body support section.

Prior to attachment of the split-leg accessory 10, the leg support section 20 is pivoted downwards, in the direction of arrow B, so that is positioned at an angle of about 90 degrees from the lower body support section 18. The lower body section 18 includes a pair of spaced, parallel side rails 24, one on either side of the lower body gig support section, to which the split-leg accessory 10 is attached, as shown in FIG. 2. The split-leg accessory comprises right and left accessory sub-assembles 26 and 28 for supporting the patient's right and left legs, respectively. The assemblies are mirror images of each other. Thus where only the right sub-assembly 26 will be described in detail, it should be appreciated that the description also applies to the left sub assembly. Each of the sub-assembles 26 and 28 is attached to one of the side rails 24. Of course, the accessory 10 could also be attached to similar side rails 30 on the upper body section 16 of the table of FIGS. 1 and 2 by first pivoting the head section 14 out of the way or side rails 32 on the head section, without pivoting the head section. In such an arrangement, the patient would be placed on the table in the opposite direction, with the head of the patient on the leg support section or lower body section. In yet another arrangement, the patient is left in the normal orientation and the accessory 10 is attached to the side rails 30 or 32 on the upper body section or head section, and used to support the patient's arms during surgery. The sub-assemblies 26,28 can be used singly, or in combination.

Figure 3:
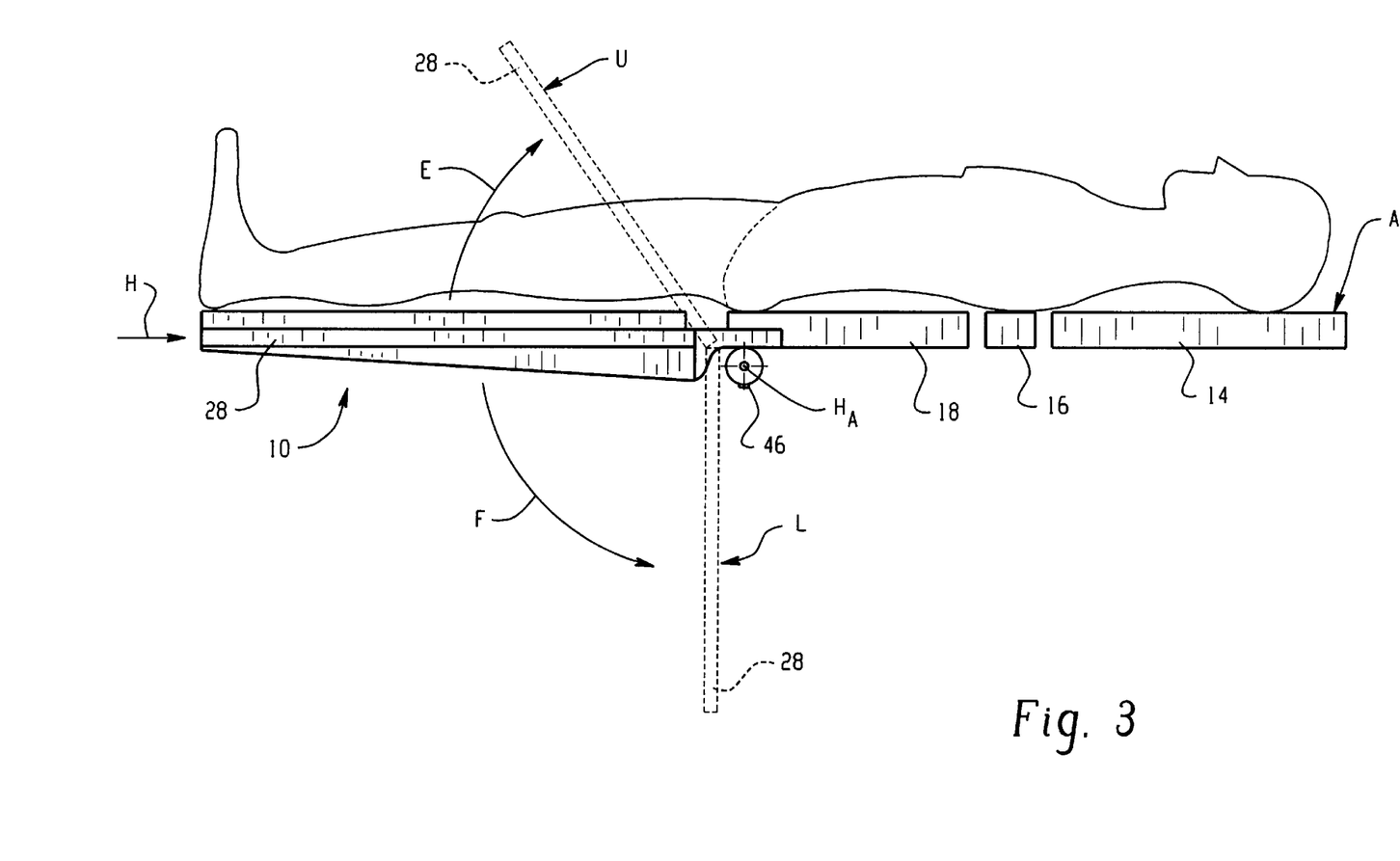
FIG. 3 is a schematic side sectional view of a patient positioned on a surgical table with the split-leg attachment of FIG. 2 shown in upper (U), lower (L), and level (H) vertical positions.
Figure 4:
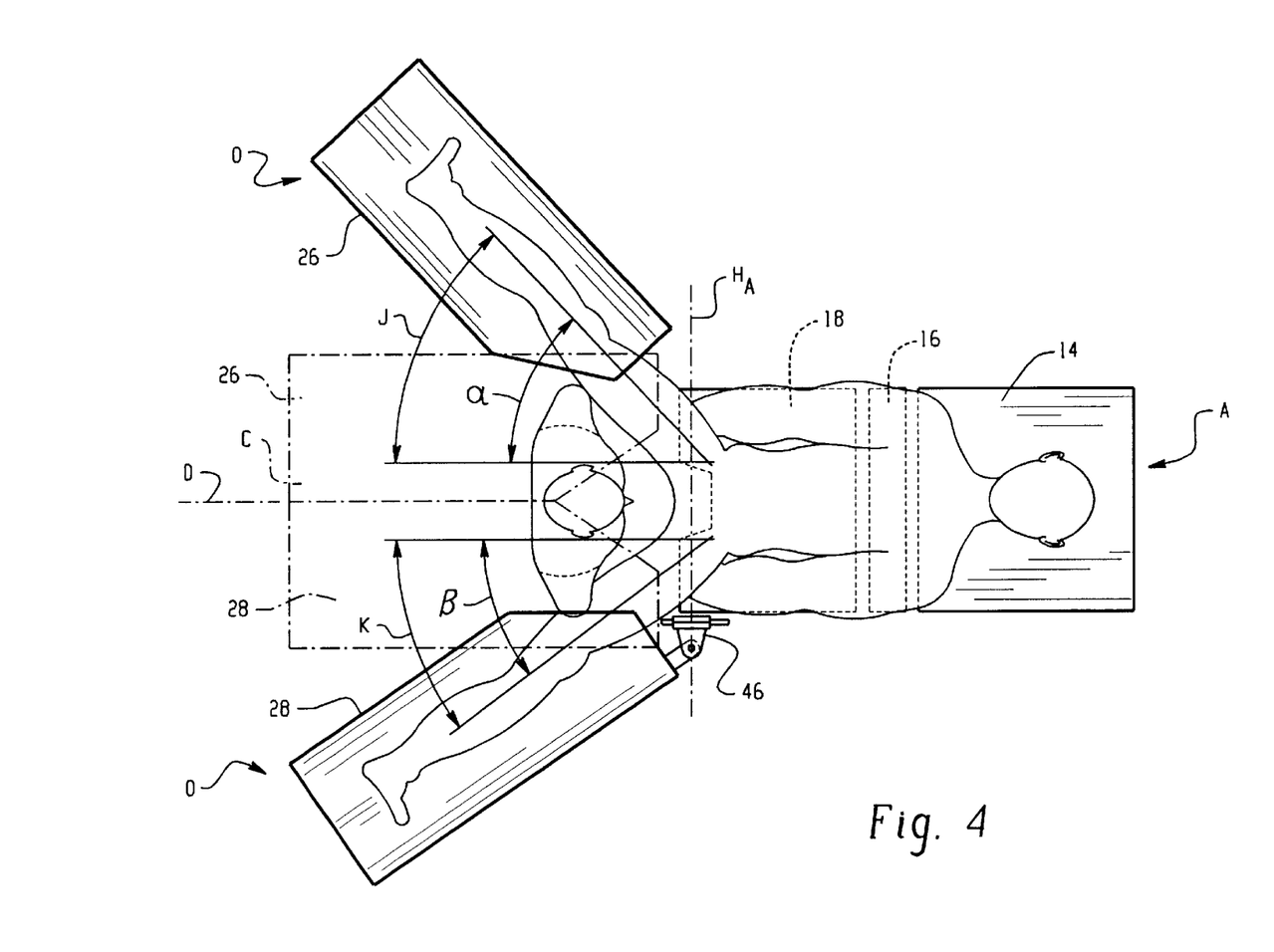
FIG. 4 is a schematic top view of view of a patient positioned on a surgical table with the split-leg accessory of FIG. 2 shown in closed and open horizontal positions.

With reference to FIGS. 3 and 4, the sub-assemblies 26,28 of the split-leg accessory 10 are pivotable about first and second mutually perpendicular axes, $H_A$ and $V_A$. Specifically, the sub-assemblies are vertically pivotable about a horizontal axis $H_A$ through the table top to raise and lower the patient's legs. As shown in FIG. 3, in which the leg section 20 of the table A is removed for clarity, the sub-assemblies can be raised in the direction of arrow E in a series of steps from a horizontal position H, shown in complete lines, in which the sub-assemblies are level with the table lower body section, to an upper position U, shown in phantom, in which the sub-assemblies are angled at approximately 45 degrees above the horizontal. The accessory can also be lowered from the horizontal position H in the direction of arrow P in a series of steps to a lower position L, shown in phantom, which is approximately 90 degrees below the horizontal. Additionally, each of the sub-assemblies 26 and 28 is separately movable, so that they may be independently lowered or raised. This is particularly beneficial for surgeries where it is desirable to lower one leg out of the way while the other leg is operated upon in the level position. Additionally, fluoroscopic imaging of an affected leg is improved since a C-arm of an imaging device is able to rotate around one leg without interference of the other leg.

With reference to FIG. 4, the sub-assemblies are also horizontally pivotable about a vertical axis $V_A$, in the direction of arrows J and K, to move them from a closed position, in which the patient's legs are lying generally parallel to one another, to an abducted, or open position in which the legs are spaced apart, and a surgeon has ready access to the patient's pelvic region. As shown in FIG. 4, the sub assemblies 26 and 28 are separately horizontally movable from a closed position C, shown by the hatched lines, to an open or abducted position O in which the right sub-assembly is at an angle a to a plane D through the patient's body, while the left assembly is at an angle β. The angles α and β are variable in a series of steps from 0 to about 52 degrees (fully abducted) and may the same or different. Thus, one of the sub assemblies may be kept in the closed position, or a slightly open position, while the other leg assembly is moved to a fully open position. In combination with the vertical adjustment of the separate sub-assemblies, the range of possible leg positions offers a wide range of operating and imaging positions for the patient's legs. For example, for laparoscopic procedures, the patient's position can be changed from a supine position for intubation and extubation to a split-leg position for and during the surgery.

Figure 5:
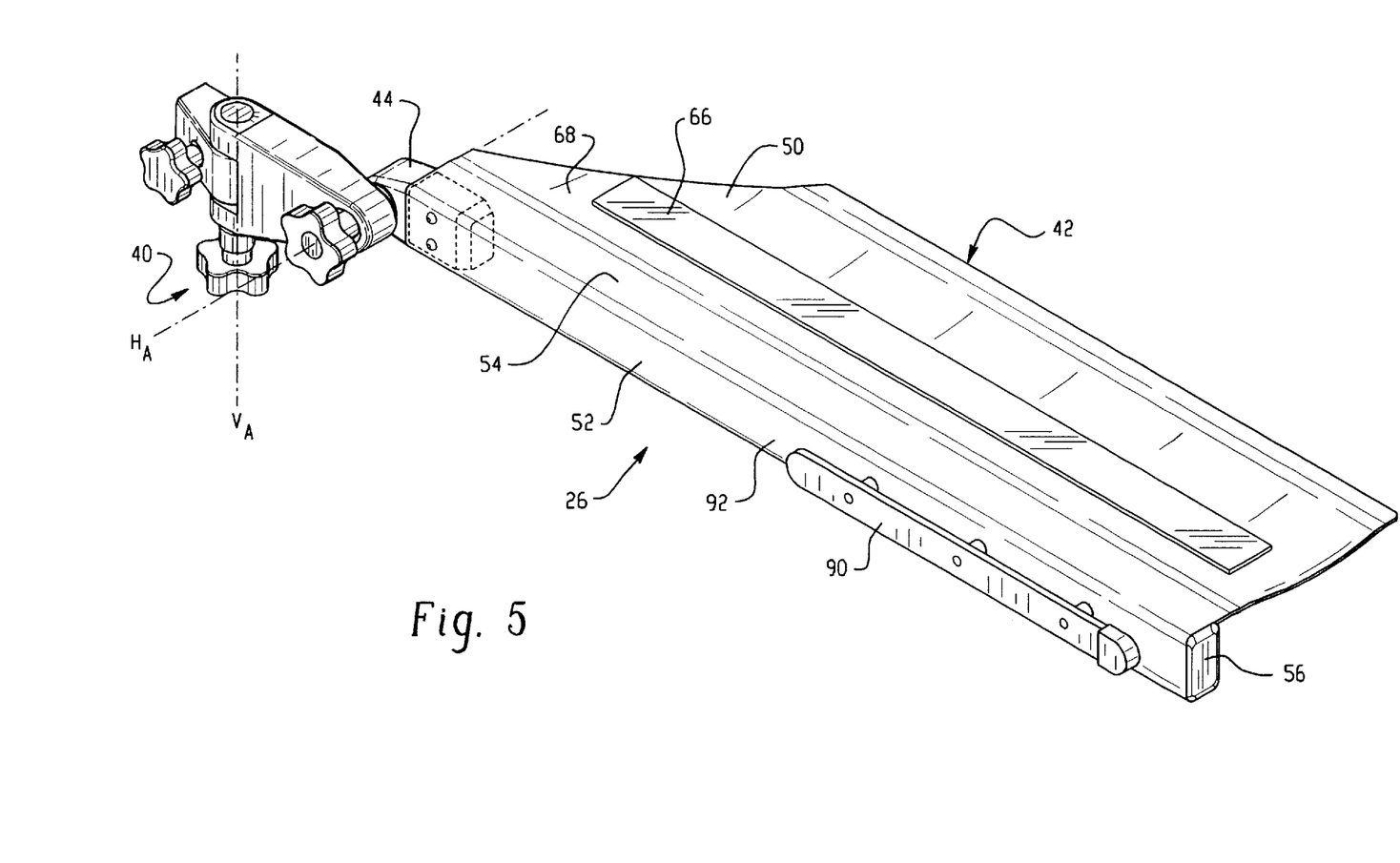
FIG. 5 is a perspective view of a right leg sub-assembly and joint assembly of the split-leg accessory of FIG. 2.
Figure 6:
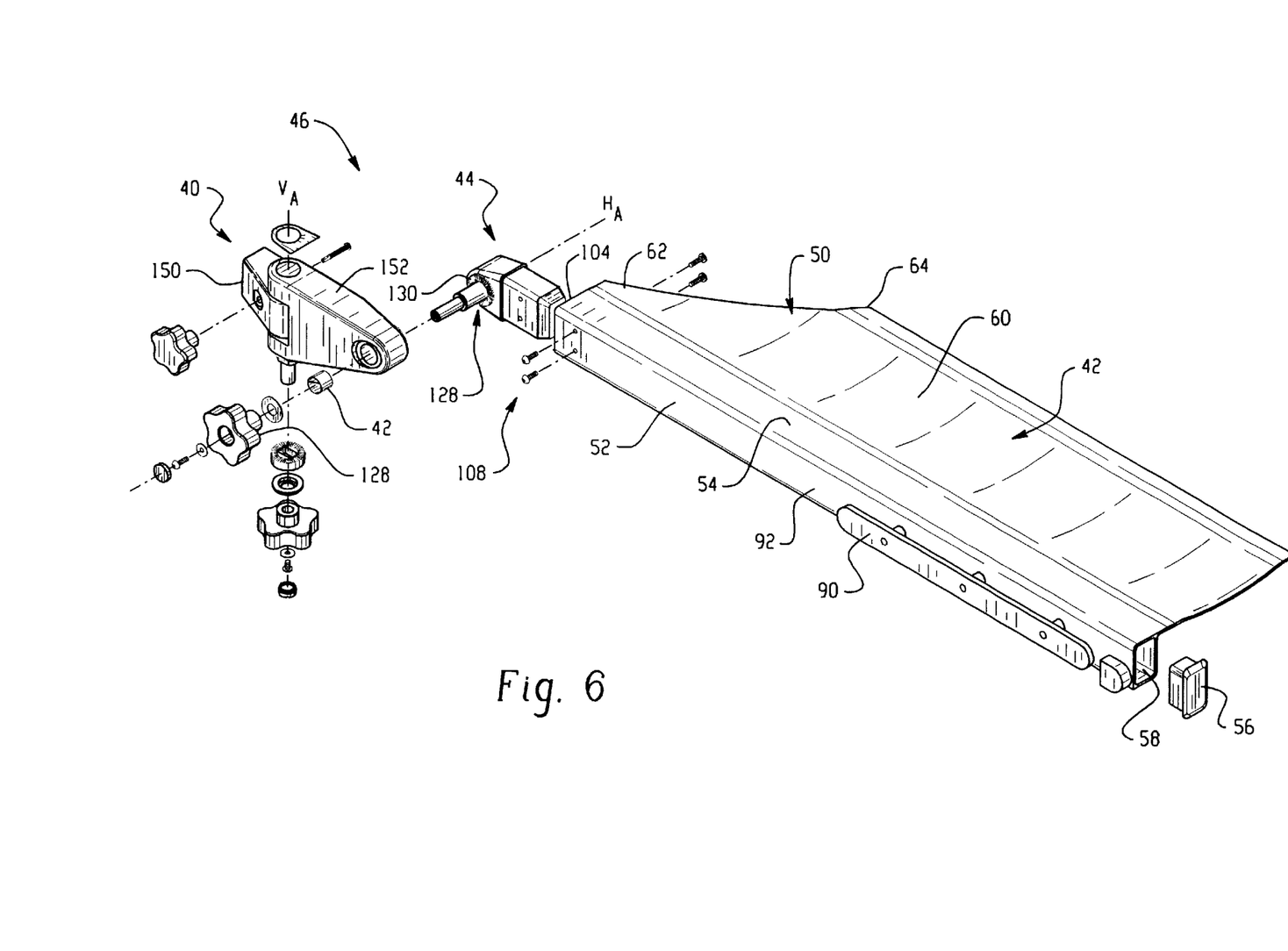
FIG. 6 is an exploded perspective view of the right leg sub-assembly and joint assembly of FIG. 5.
Figure 7:
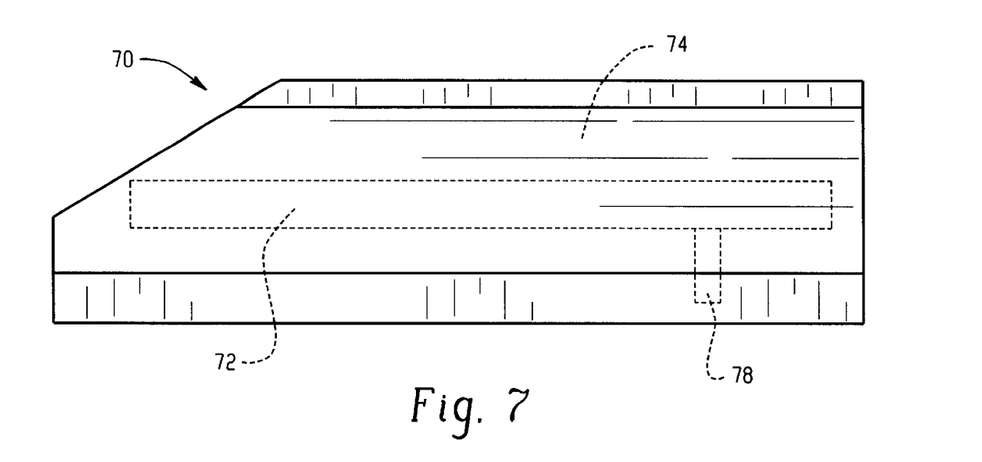
FIG. 7 is a top view of a cushioned pad for the right leg sub-assembly of FIG. 5.
Figure 8:
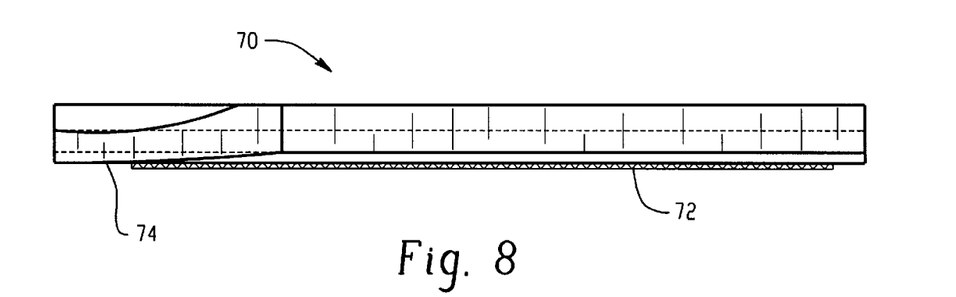
FIG. 8 is a side sectional view of the cushioned pad of FIG. 7.

With reference to FIGS. 5 and 6, each accessory sub-assembly 26, 28 includes a joint assembly 40, a leg support member or top member 42 and a cross pin assembly 44 connected between the joint assembly and the leg support member. The joint assembly 40 provides the horizontal and vertical pivotal motions of the sub-assembly, and also clamps the assembly to a suitable side rail. The cross pin assembly 44 is pivotally connected about a horizontal axis $H_A$ to the joint assembly and is joined to the top member 42. Together, the joint assembly and cross pin assembly comprise a mounting member 46. The top member 42 is radiolucent, i.e. it is formed from a radiolucent material, and is indented to cradle and support the patient's leg. By radiolucent, it is meant that the item is permeable to radiation, particularly X-rays, which are aimed at the item from any selected angle.

With particular reference to FIG. 6, the top member 42 includes a support surface 50 and an integrally-formed torque tube or tubular member 52, which are both formed from a radiolucent material, such as carbon fiber. The support surface 50 is shaped to receive the patient's leg and foot. The support surface thus supports an upper portion of patient's leg, above the knee, a lower portion of the patient's leg, below the knee, the ankle, and the foot, allowing radiological examination of all these portions of the leg through the radiolucent support surface 50. The torque tube 52 is formed in the shape of a hollow rectangular box, the upper surface of which is provided by an outer edge 54 of the support surface. The torque tube provides rigidity to the support surface, and extends along the length of the support surface, along an outer horizontal side thereof. An end cap 56, formed from a radiolucent material, such as polyurethane, seals off an open, distal end 58 of the torque tube. The support surface 50 and torque tube 52 are preferably molded as a single piece using conventional carbon fiber forming techniques. Specifically, several layers of carbon fibers are stacked to form a felt and impregnated with a resin material. The impregnated carbon fiber felt is heat molded to cause the resin to flow through the felt and cure in the desired shape. Such a unitary construction allows the accessory 10, in combination with the table A, to support a patient of at least 225 kg in weight. The accessory is also light weight for moving to and from the table. Preferably each sub-assembly 26, 28 weighs no more than about 7 kg.

The support surface 50 includes an indented region or trough 60, which extends axially along its length for centering the patient's leg and minimizing movement of the leg during surgery. A proximate end 62 of the support surface, closest to the table, is angled away from the table, adjacent an inner side 64, to provide a generally triangular cut-out portion. This provides greater access for the surgeon, as shown in FIG. 4.

Figure 9:
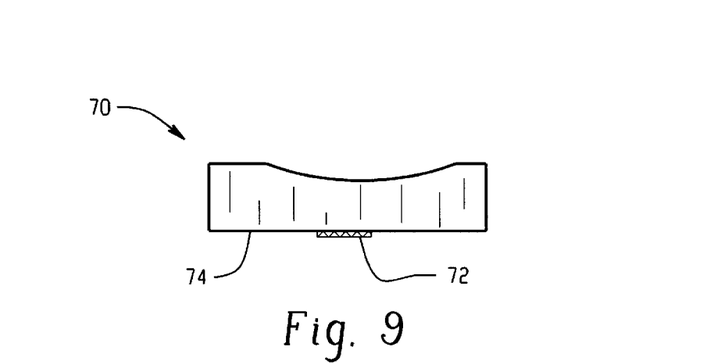
FIG. 9 is a cross-sectional view of the cushioned pad of FIG. 7.

A strip 66 of hook and latch cloth, such as Velcro®, is axially adhered to an upper surface 68 of the support surface 50 (FIG. 5). A cushioned pad 70 with a matching piece of hook and latch cloth 72 attached to a lower surface 74 of the pad is received on the support surface (FIGS. 2 and 7–9). The pad 70 is similarly indented to the support surface for cradling the patient's leg and cut away at a proximate end 76 for access by the surgeon. Optionally, a conductive label 78 is attached to a lower surface of the pad. The pad is formed from a radiolucent material, such as a polyurethane foam, and may be covered with a radiolucent fabric, such as LECTROLYTE Synergy fabric. The pad shown in FIG. 9 is flexible, such that its lower surface 74 conforms to the shape of the trough 60 in the top member. It is also contemplated that the pad 70 be formed with a curved lower surface.

With reference once more to FIGS. 5 and 6, a side rail 90 is attached to an outer vertical side 92 of the torque tube 52. The side rail is used for selective attachment of accessories, such as medical equipment, and the like, during surgery. The side rail is formed from a radiolucent material, such as carbon fiber, which is strong enough to support the weight of the accessories.

With reference to FIGS. 6 and 10–13, the cross pin assembly 44 is formed from conventional materials, such as aluminum or stainless steel. The cross pin assembly 44 includes a body portion 100 which is stepped inward, adjacent one end to form a box-shaped mounting portion 102. The mounting portion is shaped to be received snugly in a proximal end 104 of the torque tube 52. The mounting portion preferably extends about 4–6 cm into the interior of the torque tube as shown in phantom in FIG. 5 and is securely adhered to the inner surface of the torque tube with an adhesive. Additionally, fixing members 108, such as bolts or screws, are also used to attach the torque tube to the mounting portion, as shown in FIG. 6.

Figure 10:
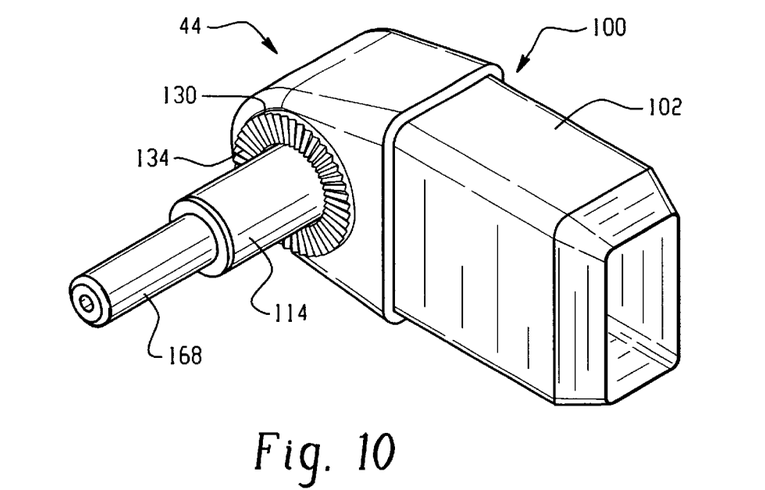
FIG. 10 is an enlarged perspective view of the cross pin assembly of FIG. 5.
Figure 11:
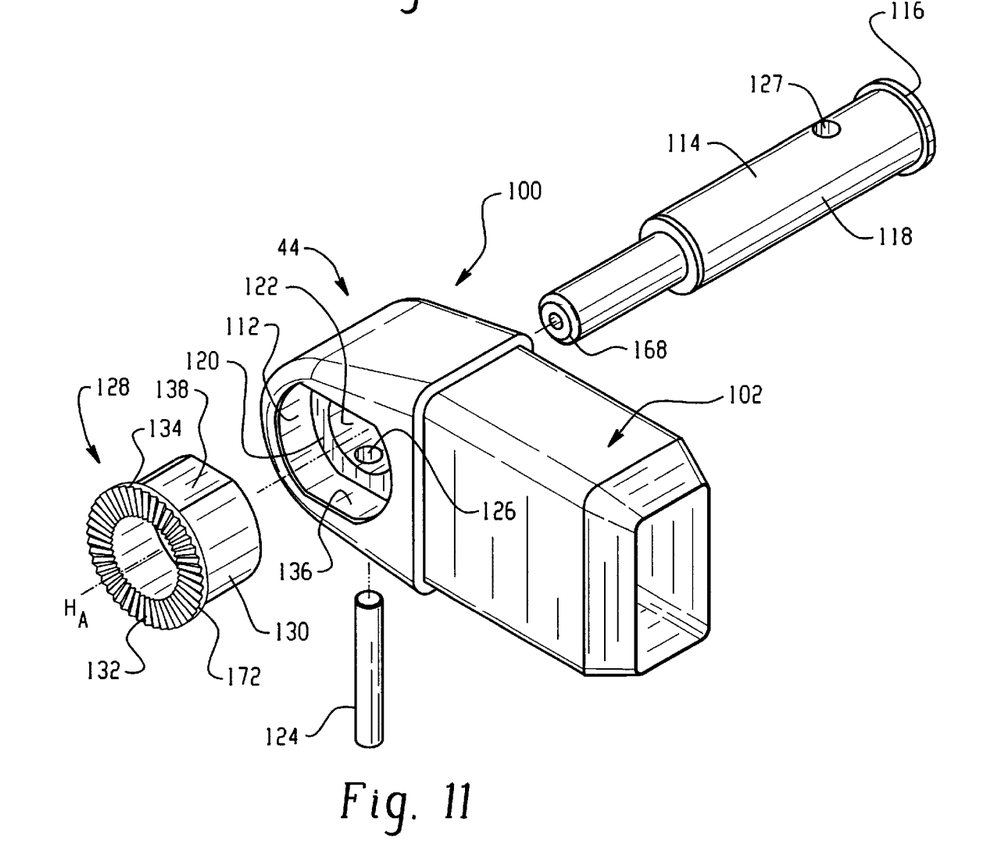
FIG. 11 is an exploded perspective view of the cross pin assembly of FIG. 10.
Figure 12:
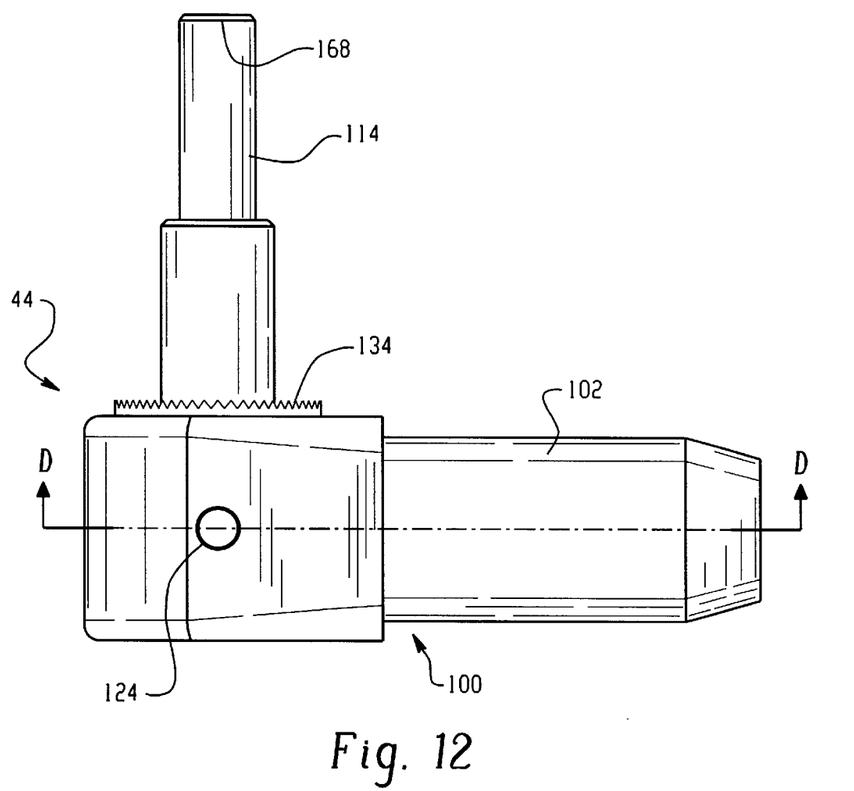
FIG. 12 is a schematic side view of the cross pin assembly of FIG. 10.
Figure 13:
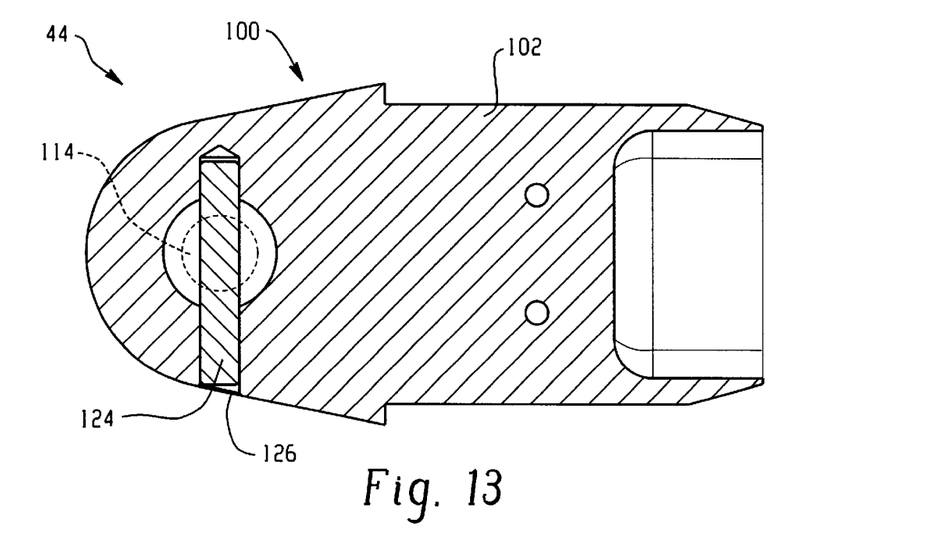
FIG. 13 is a sectional view through D—D of FIG. 12.

With particular reference to FIGS. 10 and 11, the other end of the body portion 100 includes a laterally extending bore 112 extending therethrough. A first, horizontally extending pivot pin 114 is received through the bore. A circumferential flange 116 at a distal end 118 of the pivot pin engages a stepped portion or shelf 120 which extends inwardly into the bore 112, perpendicular to the bore. A circular opening 122 in the stepped portion receives the first pivot pin, other than the flange 116, therethrough. When inserted into the opening, the first pivot pin extends laterally from the body portion to provide a horizontal axis $H_A$ for pivoting of the cross pin assembly 44 and the attached top member 42 therearound. As shown in FIGS. 11, 12, and 13, a vertically extending, first locking pin 124 locks the first pivot pin 114 to the body 100 of the cross pin assembly. Specifically, the first locking pin is inserted through an opening 126 in a lower surface of the cross pin assembly 42, enters the bore 112 of the cross pin assembly and passes trough a vertically extending bore 127 in the first pivot pin.

A first locking assembly 128 locks the cross pin assembly 44 to the joint assembly 40 in one of a selected number of rotational positions. The first locking assembly 128 includes a generally cylindrical first gear member 130 with a central bore 132. The gear member is received in the bore of the body portion such that a rear surface of the gear member rests on the stepped portion 120 and an annular ratcheted gear disc 134 protrudes outward from the body portion. The gear member 130 is rotatably connected with the cross pin assembly. Specifically, the gear member is shaped to be received in the body portion bore 112. Both the bore and gear member include flattened portions 136 and 138, respectively, which prevent the gear member from rotating relative to the bore. The first pivot pin 114 is received through the gear member bore 132, as shown in FIG. 10.

With reference to FIGS. 6, 14, 15, and 16, the joint assembly 40 includes a clamping portion 150, for clamping the joint assembly to the side rail 24 of the surgical table, and a pivoting portion 152, which is pivotally connected to the clamping portion 150 by a second, vertically extending pivot pin 154. The second pivot pin 154 allows the pivoting portion 152 to pivot horizontally about a vertical axis $V_A$ through the second pivot pin as shown by arrow J. The pivoting portion is also pivotally connected to the cross pin assembly 44 by the first pivot pin 114. The first pivot pin therefore allows the sub-assembly 26 to pivot about a horizontal axis $H_A$ through the first pivot pin for raising and lowering the patient's legs, while the second pivot pin 154, which is perpendicular to the first pivot pin, allows the sub assembly to pivot about a vertical axis $V_A$ through the second pivot pin, for abduction of the patient's legs.

Figure 15:
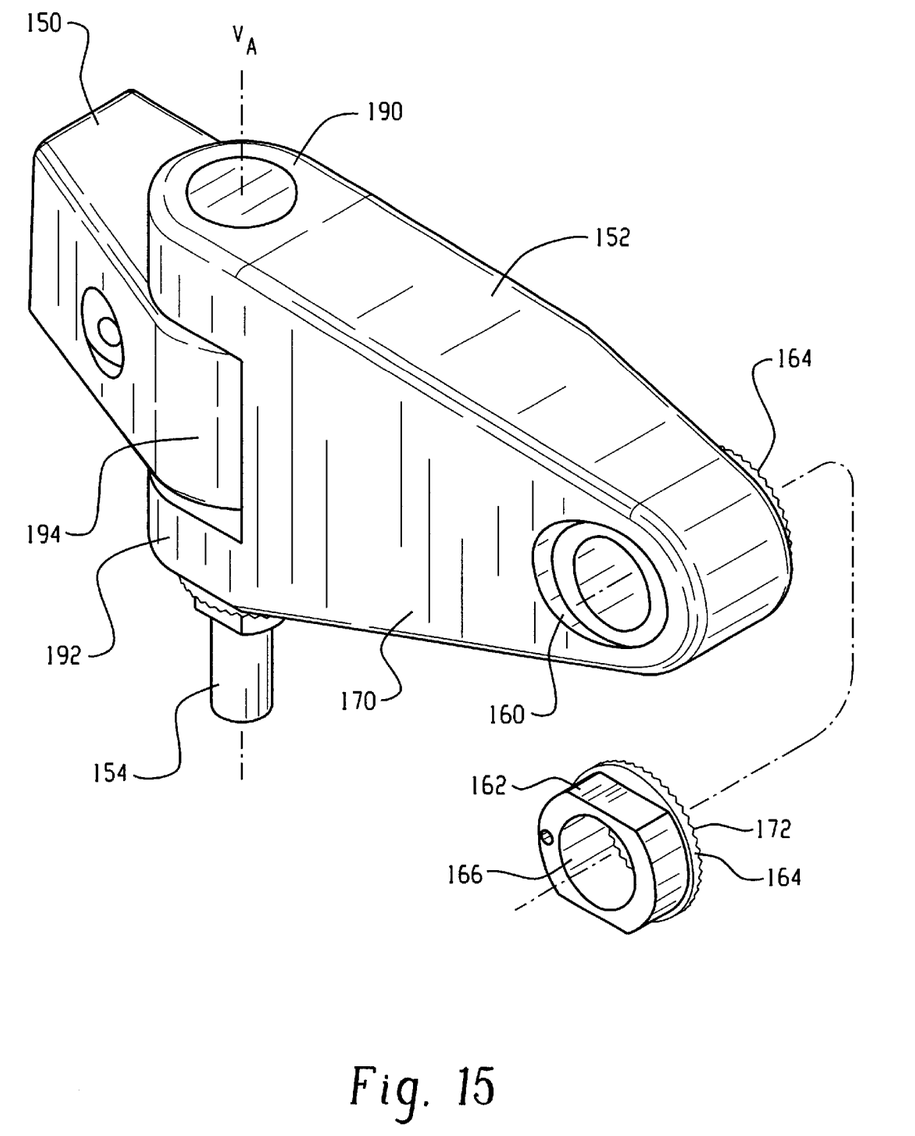
FIG. 15 is an enlarged, partially exploded perspective view of the joint assembly of FIG. 5.

With particular reference to FIG. 15, the pivoting portion 152 of the joint assembly 40 includes a horizontally extending bore 160, similar to the bore 112 in the cross pin assembly. The first locking assembly 128 also includes a second gear member 162, which is similar to the first gear member 130. The second gear member is received in an inward facing side of the bore 160 such that an annular ratcheted gear disc 164, which matches the first gear disc 134 on the first gear member 130, protrudes outward from the pivoting portion toward the cross pin assembly 44. The second gear member 162, like the first gear member, is rotatably coupled to the pivoting portion 152 and is not free to rotate within the pivot portion bore, but is held in a fixed position in the pivot portion bore by matching flattened portions, similar to those on the cross pin assembly bore and first gear member. The second gear member 162 includes an annular bore 166 which is shaped to receive a distal end 168 of the first pivot pin therethrough. Accordingly, when the sub-assembly 26 is fully assembled, the first pivot pin first passes through the body portion 100, then through the first and second gear members 130,162 and through the pivoting member 152, such that it protrudes beyond an outward facing side 170 of the pivoting member.

To position the sub assembly 26 in a selected vertical rotational position relative to a horizontal plane, the locking assembly 128 locks the cross pin assembly 44 to the pivoting member in one of a selected number of rotational positions. Specifically, the gear disc 134 of the first gear member 130 is engaged with the gear disc 164 of the second gear member 162. The number of possible rotational positions is determined, in part, by the spacing of the ratchets 172 on the first and second gear discs 134,164. Preferably, between 10 and 30, or more, such positions are provided.

Figure 14:
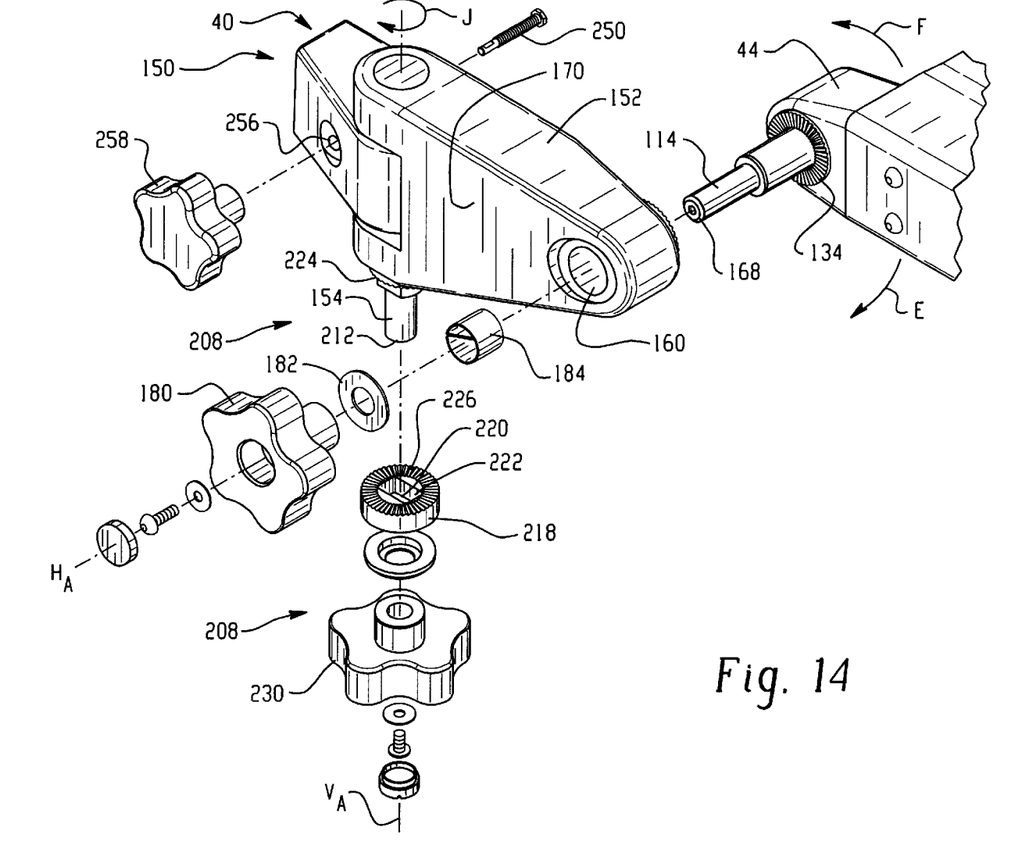
FIG. 14 is an enlarged, exploded perspective view of the joint assembly of FIG. 6.

With reference to FIG. 14, the first locking assembly 128 also includes a first, threaded locking nut 180. To engage the first and second gear discs, the locking nut 180 is tightened over the distal end 168 of the first pivot pin 114 until the first and second gear discs are brought into engagement, thereby locking the sub-assembly 26 in a preselected vertical rotational position. Preferably, a washer 182, between the first locking nut and the pivot pin 114, and a bearing 184 between the pivot pin and the pivot member bore, assist in positioning and engagement.

Figure 16:
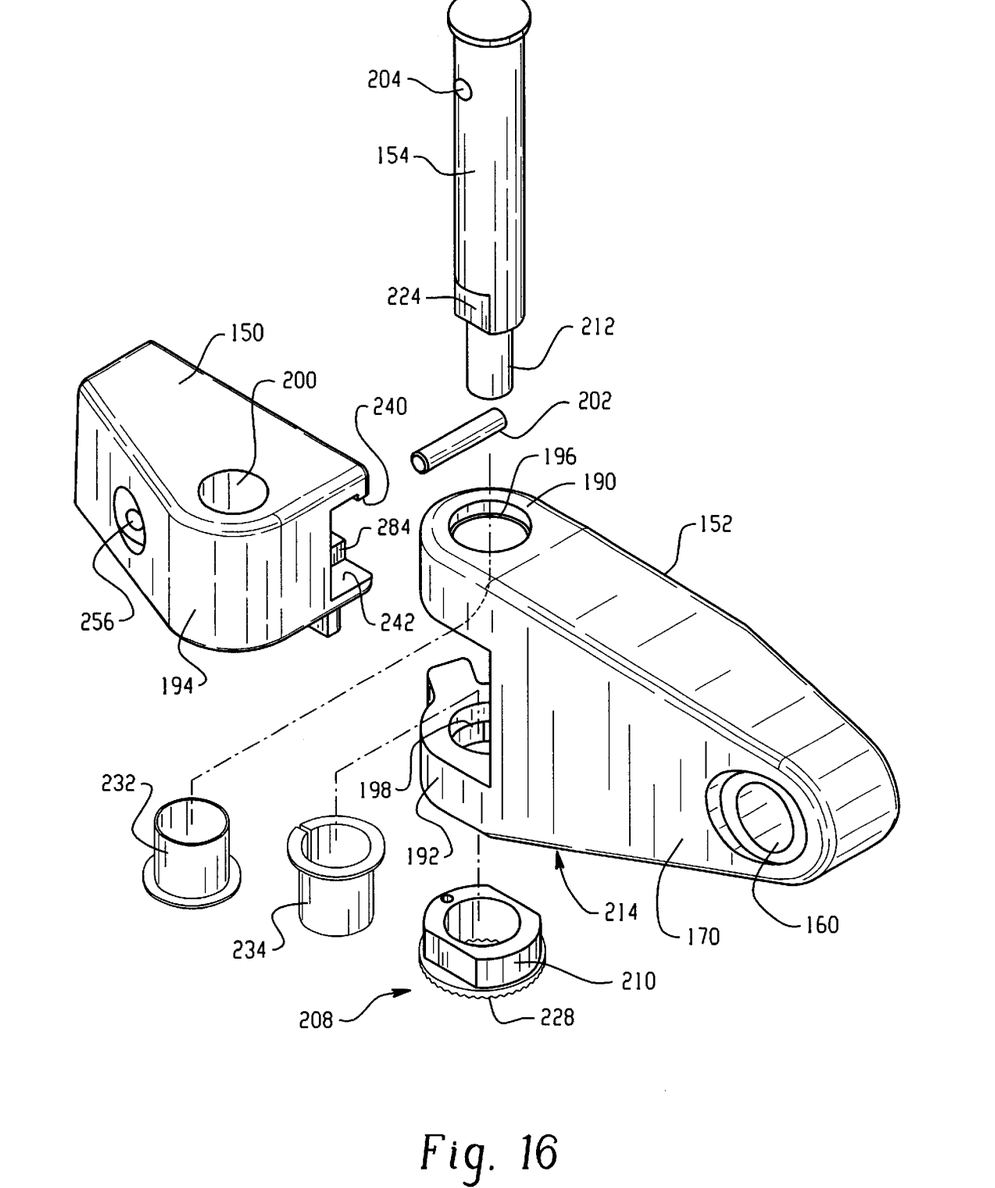
FIG. 16 is an exploded perspective view of the joint assembly of FIG. 14.

With reference to FIGS. 14 and 16, a similar arrangement of gear discs allows the clamping member 150 to be locked to the pivoting member 152 in one of a preselected number of horizontal rotational positions. With particular reference to FIG. 16, the pivoting member 152 includes upper and lower horizontally extending, parallel flanges 190 and 192, respectively, which are spaced to receive a mating portion 194 of the clamping member therebetween. The flanges have vertically extending bores 196 and 198, respectively, which are positioned to align with a corresponding bore 200 in the clamping portion. The second pivot pin 154 is rotatably coupled to the clamping portion by a horizontally extending, second locking pin 202. The second locking pin is received through a horizontal bore 204 in the second pivot pin and passes through a corresponding horizontal bore (not shown) in the clamping portion mating portion 194 and passes transversely through the clamping portion bore 200 to rotatably lock the pivot pin to the clamping portion.

A second locking assembly 208 includes a third stationary gear member 210, similar to the first and second gear members, which is received at a lower end of the lower flange bore 198. The third gear member 210 remains stationary relative to the pivoting member 152. The second pivot pin 154 is received through the upper flange bore 196, the clamping member bore, the lower flange bore 198 and the third gear member 210 such that a distal end 212 of the second pivot pin projects below a lower surface 214 of the pivoting member. The second locking assembly 208 also includes a fourth gear member 218, best shown in FIG. 14, which is received on the distal end 212 of the second pivot pin such that it remains stationary with respect to the pivot pin. Specifically, an internal bore 220 of the fourth gear member includes a pair of stepped portions 222 which engage similar stepped portions 224 on the distal end of the second pivot pin. A gear disc 226 on the fourth gear member faces upwardly to mate with a corresponding gear disc 228 on the third gear member 210.

To lock the clamping member 150 to the pivoting member 152 in one of a selected number of horizontal rotational positions, the third and fourth gear members are brought into engagement. Specifically, a second, threaded locking nut 230 is tightened onto the distal end 212 of the second pivot pin 154 until the gear discs 226 and 228 on the third and fourth gear members engage in a locking arrangement.

Optionally, bearings 232 and 234 are inserted between the flange bores 196, 198 and the second pivot pin 154.

Figure 17:
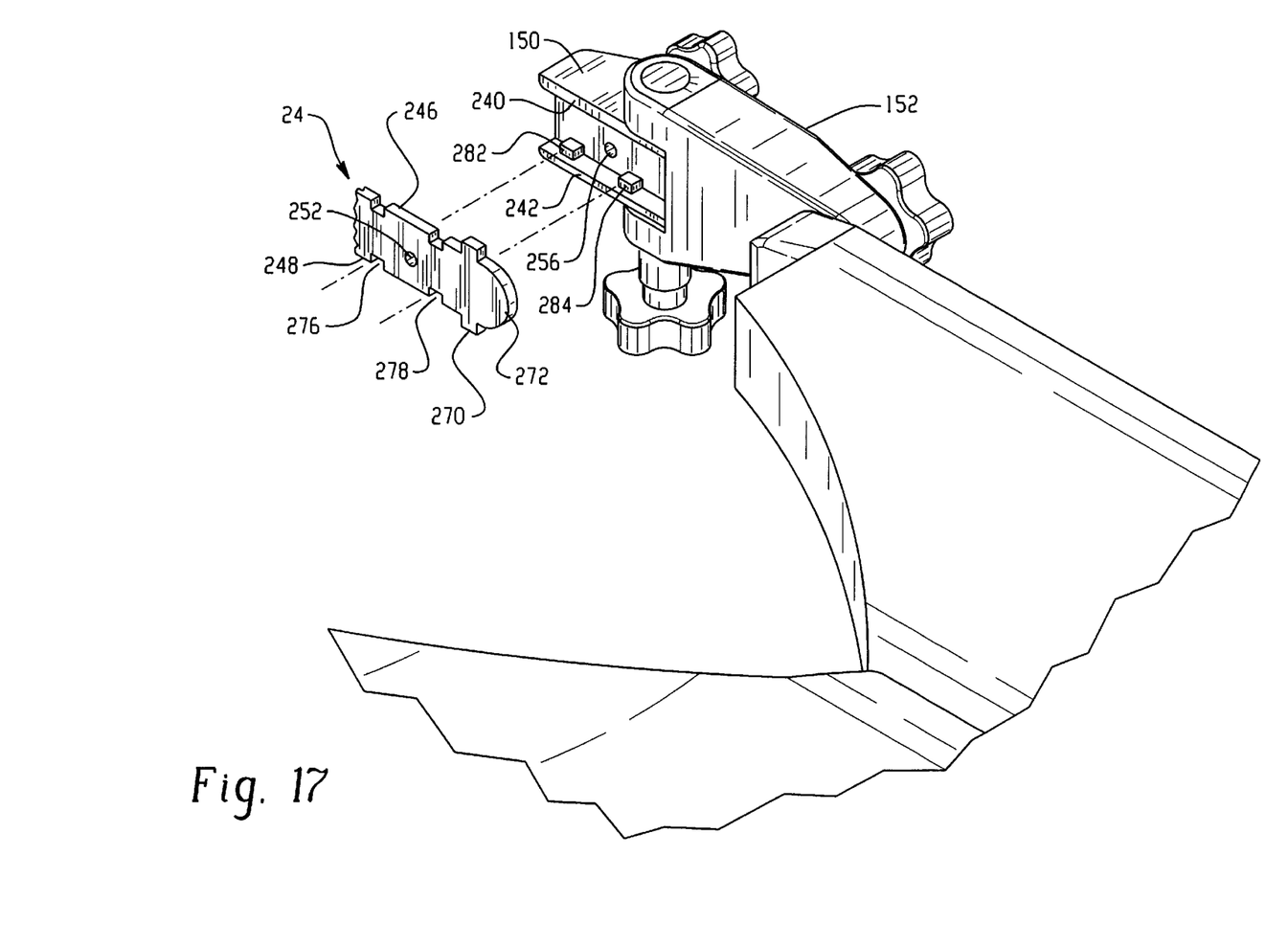
FIG. 17 is a perspective view of the side rail of the surgical table of FIG. 1 and a left leg sub-assembly of the split-leg accessory of FIG. 2 prior to attachment; and, FIG. 18 is a perspective view of a second embodiment of a sub-assembly of a split-leg accessory according to the present invention.

With reference to FIGS. 14, 16 and 17, the clamping member 150 is configured for clamping to the side rail 24 of the surgical table by a suitable clamping arrangement. The clamping member includes upper and lower rails 240 and 242 which are spaced to slide along adjacent, upper and lower edges 246 and 248 of the side rail, respectively. The clamping member is clamped to the side rail 24 with one or more suitable fixing members 250, such as a bolt or screw, best shown in FIG. 14. As shown in FIGS. 16 and 17, a threaded bolt 250 is received through an aperture 252 in the side rail and a corresponding aperture 256 in the clamping member. A third locking nut 258 is tightened onto a distal end of the bolt to hold the clamping member rigidly against the side rail 24.

FIGS. 16 and 17 show a preferred clamping member suited to attachment to the type of side rail having a flange 270 adjacent an end 272 of the side rail which is designed to prevent accessories from sliding off the end of the side rail. Specifically, the side rail 24 includes first and second spaced notches 276 and 278, which are cut into the lower edge 248 of the side rail adjacent the flange 270. Horizontally spaced first and second tabs 282 and 284, which extend vertically from the lower rail 242 of the clamping member 150, are shaped and positioned to be received in the corresponding notches 276, 278. To position the clamping member on the side rail, the clamping member is first aligned so that the tabs are received in the notches and then the clamping member is slid along the side rail until the apertures 252,256 are aligned. The clamping member is then bolted to the side rail as previously described.

Figure 18:
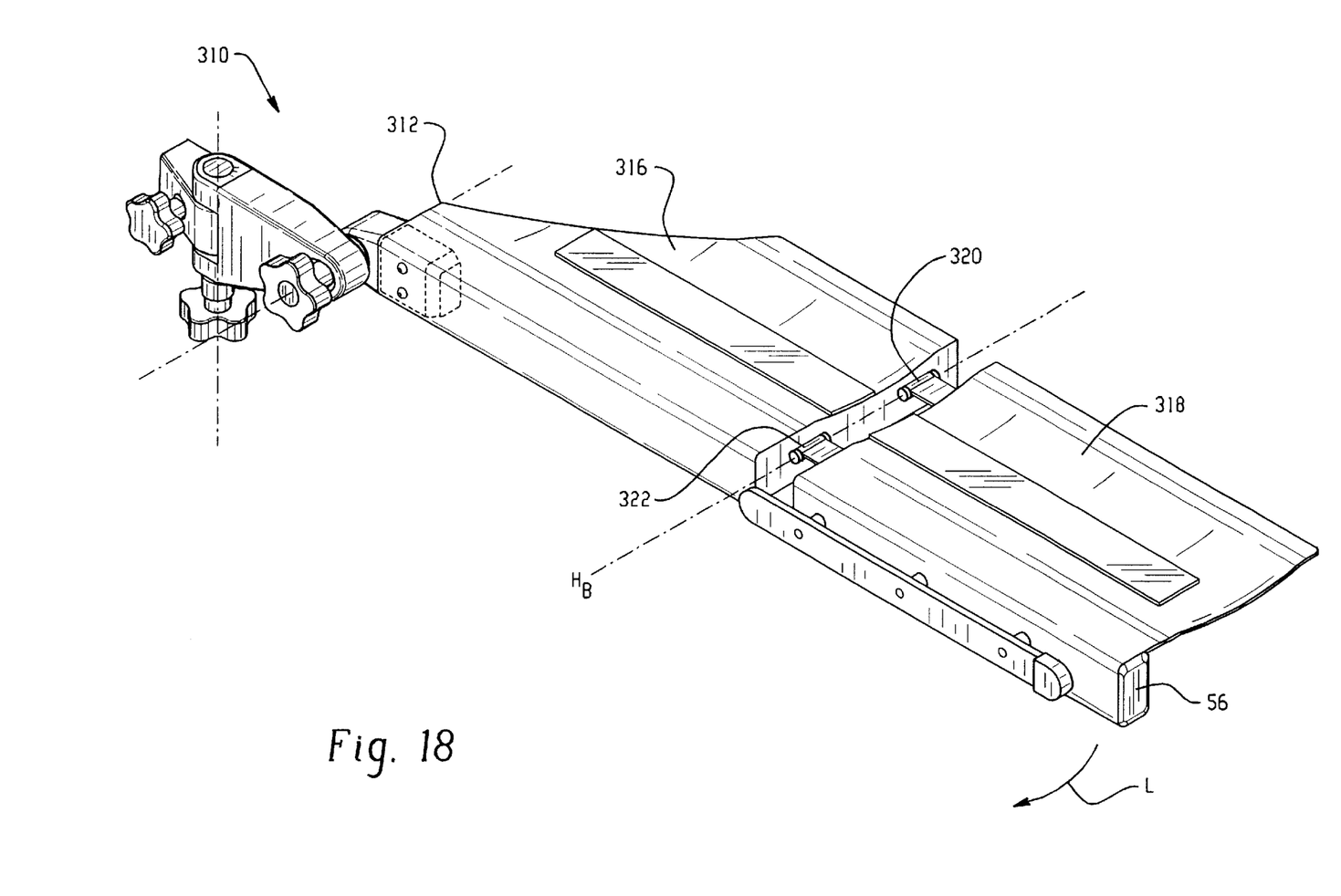

With reference to FIG. 18, an alternative embodiment of a split leg accessory 310 is shown. The accessory is identical in all respects to the assembly 10 of FIGS. 1–17, except in that each of a pair of sub-assemblies 312 comprises first and second top member portions, 316 and 318, for cradling upper and lower portions of a patient's legs, respectively. The first and second top member portions are pivotally connected at pivot points 320 and 322, corresponding approximately to the position of a patient's knee, such that the second top member portion 318 is vertically rotatable, as shown by arrow L, about a horizontal axis $H_B$ through the pivot points, for lowering the patient's lower leg from a position in which the lower and upper leg portions are aligned, to a position in which the lower leg extends downwardly away from the knee joint. Similar locking mechanisms to those described for the pivoting member of the first embodiment are included for locking the first and second top portions in one of a selected number of positions.

Of course, a pair of cushion pads, rather than a single cushion pad are provided for each of the sub-assemblies. It is also contemplated that more than two top member portions could be provided.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A surgical table for supporting a patient during the performance of a surgical procedure, the table comprising:
   a base;
   a table top mounted on the base for supporting an upper portion of the patient's body; and
   at least one leg support sub-assembly pivotally mounted to the table top, the at least one leg support sub-assembly including:
      a support member for supporting a patient's leg, the support member including a support surface formed from a radiolucent material, and
      a mounting member which pivotally connects the support member to the table top, the mounting member including a joint assembly for releasably mounting the leg support sub-assembly to the table top, the joint assembly being configured for clamping to a side rail of the table top.

2. The table of claim 1, wherein the at least one leg support sub-assembly is pivotable about two mutually perpendicular axes.

3. The table of claim 1, wherein the table includes:
   two leg support assemblies.

4. The table of claim 3, wherein the leg support sub-assemblies are pivotable between a closed position, in which the supporting surfaces are adjacent, to a fully abducted position, in which the patient's legs are spaced apart.

5. The table of claim 3, wherein the leg support sub-assemblies are each independently pivotable about a horizontal axis between a lowered position, in which the patient's leg is below the patient's body to an upper position, in which the patient's leg is elevated above the patient's body.

6. The table of claim 1, wherein the support surface is formed from carbon fiber.

7. The table of claim 1, wherein the support surface defines a trough, which is shaped for receiving the patient's leg.

8. The table of claim 1, wherein the support surface supports an upper portion of the patient's leg, above the patient's knee, and a lower portion of the patient's leg, below the patient's knee.

9. The table of claim 1, further including a radiolucent pad, received on the support member, for cushioning the patient's leg.

10. A surgical table for supporting a patient during the performance of a surgical procedure, the table comprising:
    a base;
    a table top mounted on the base for supporting an upper portion of the patient's body; and
    at least one leg support sub-assembly pivotally mounted to the table top, the at least one leg support sub-assembly including:
       a support member for supporting a patient's leg, the support member including:
          a support surface formed from a radiolucent material, and
          a rigid tubular member which supports the support surface, and
       a mounting member which pivotally connects the support member to the table top.

11. The table of claim 10, wherein the tubular member receives a body portion of the mounting member at least partly therethrough for connecting the support member with the mounting member.

12. The table of claim 10, wherein the tubular member and the support surface are both formed from a radiolucent material.

13. A surgical table for supporting a patient, the table comprising:
    a base;
    a table top mounted on the base for supporting a portion of the patient's body;
    at least one leg support sub-assembly mounted to the table top, the at least one leg support sub-assembly including:
       a support surface for supporting a patient's leg,
       a rigid structural member which supports the support surface, the rigid structural member and the support surface being formed as a single piece of radiolucent material.

14. A removable accessory for a surgical table, the accessory comprising:
    a radiolucent support member for supporting upper and lower portions of a patient's leg; and
    a mounting member for selectively connecting the support member to the surgical table and removing the support member from the surgical table, the mounting member including a clamping portion for clamping to the surgical table, the support member including a pivot for selective pivoting the support member relative to the table.

15. An accessory for a surgical table, the accessory comprising:
    a support member for supporting a patient's leg, the support member including a support surface formed from a radiolucent material, which supports upper and lower portions of the patient's leg; and
    a mounting member adapted for selective clamping the support member on to a side rail of a top of the table, the mounting member enabling selective pivoting of the support member relative to the table.

16. An accessory for a surgical table, the accessory comprising:
    a support member for supporting a patient's leg, the support member including:
       a support surface formed from a radiolucent material, which supports upper and lower portions of the patient's leg, and
       an integrally formed rigid tubular member which supports the support surface; and
    a mounting member for selectively mounting the support member to the surgical table, the mounting member enabling selective pivoting of the support member relative to the table.

17. The accessory of claim 16, wherein the tubular member receives a body portion of the mounting member at least partly therethrough for connecting the support member with the mounting member.

* * * * *